(12) United States Patent
Webb

(10) Patent No.: US 10,939,994 B2
(45) Date of Patent: Mar. 9, 2021

(54) COLLAPSIBLE CAVITIES WITHIN SUSPENSION SYSTEMS FOR INTRA-OCULAR LENSES

(71) Applicant: Ventura Holdings Ltd., Langley (CA)

(72) Inventor: Garth T. Webb, Langley (CA)

(73) Assignee: VENTURA HOLDINGS LTD., Langley (CA)

( * ) Notice: Subject to any disclaimer, the term of this patent is extended or adjusted under 35 U.S.C. 154(b) by 317 days.

(21) Appl. No.: 16/095,148

(22) PCT Filed: May 24, 2017

(86) PCT No.: PCT/CA2017/050623
§ 371 (c)(1),
(2) Date: Oct. 19, 2018

(87) PCT Pub. No.: WO2017/181295
PCT Pub. Date: Oct. 26, 2017

(65) Prior Publication Data
US 2020/0054443 A1 Feb. 20, 2020

Related U.S. Application Data

(60) Provisional application No. 62/341,430, filed on May 25, 2016.

(30) Foreign Application Priority Data

Apr. 22, 2016 (CA) ..................................... 2928056

(51) Int. Cl.
*A61F 2/16* (2006.01)

(52) U.S. Cl.
CPC .......... *A61F 2/1624* (2013.01); *A61F 2/1635* (2013.01); *A61F 2002/1682* (2015.04); *A61F 2002/16905* (2015.04)

(58) Field of Classification Search
CPC ............ A61F 2/1624; A61F 2002/1682; A61F 2002/16905
See application file for complete search history.

(56) References Cited

U.S. PATENT DOCUMENTS

| | | | |
|---|---|---|---|
| 4,585,457 | A | 4/1986 | Kalb |
| 4,710,194 | A | 12/1987 | Kelman |
| 4,750,904 | A | 6/1988 | Price |
| 4,892,543 | A | 1/1990 | Turley |
| 4,932,966 | A | 6/1990 | Christie et al. |
| 5,026,393 | A | 6/1991 | Mackool |

(Continued)

FOREIGN PATENT DOCUMENTS

| | | |
|---|---|---|
| CA | 1192351 A | 8/1985 |
| CA | 2630781 A1 | 5/2008 |

(Continued)

*Primary Examiner* — David H Willse
*Assistant Examiner* — Tiffany P Shipmon
(74) *Attorney, Agent, or Firm* — Oyen Wiggs Green & Mutala LLP

(57) ABSTRACT

A suspension system for suspending an intra-ocular lens in the lens capsule of an eye has one or more collapsible cavities formed in the suspension system, each having at least one opening communicating the interior of the cavity with fluid from the interior of the eye, wherein the walls of the cavity exhibit sufficient structural elasticity that they return to their habitual shapes after being compressed by external force.

17 Claims, 17 Drawing Sheets

(56) References Cited

U.S. PATENT DOCUMENTS

| | | |
|---|---|---|
| 5,476,514 A | 12/1995 | Cumming |
| 5,496,366 A | 3/1996 | Cumming |
| D395,512 S | 6/1998 | Korenfeld |
| 7,755,840 B2 | 7/2010 | Batchko et al. |
| 7,981,155 B2 | 7/2011 | Cumming |
| 8,064,142 B2 | 11/2011 | Batchko et al. |
| D688,801 S | 8/2013 | Doraiswamy et al. |
| D689,611 S | 9/2013 | Doraiswamy et al. |
| D691,273 S | 10/2013 | Doraiswamy et al. |
| 8,551,164 B2 | 10/2013 | Willis et al. |
| D699,851 S | 2/2014 | Doraiswamy et al. |
| D702,346 S | 4/2014 | Ben Nun |
| D728,789 S | 5/2015 | Doraiswamy et al. |
| D729,390 S | 5/2015 | Doraiswamy et al. |
| 9,204,962 B2 | 12/2015 | Silvestrini |
| 9,427,922 B2 | 8/2016 | Reboul et al. |
| 2003/0109926 A1 | 6/2003 | Portney |
| 2003/0158588 A1 | 8/2003 | Rizzo et al. |
| 2005/0216080 A1 | 9/2005 | Snyder |
| 2007/0118216 A1 | 5/2007 | Pynson |
| 2008/0015689 A1 | 1/2008 | Esch et al. |
| 2009/0030514 A1 | 1/2009 | Niwa et al. |
| 2009/0264998 A1 | 10/2009 | Mentak et al. |
| 2010/0179653 A1 | 7/2010 | Argento et al. |
| 2010/0231783 A1 | 9/2010 | Büeler et al. |
| 2011/0160852 A1 | 6/2011 | Mentak et al. |
| 2011/0224788 A1 | 9/2011 | Webb |
| 2013/0176628 A1 | 7/2013 | Batchko et al. |
| 2014/0222013 A1 | 8/2014 | Argal et al. |
| 2014/0368789 A1 | 12/2014 | Webb |
| 2015/0055084 A1 | 2/2015 | Stevens et al. |

FOREIGN PATENT DOCUMENTS

| | | |
|---|---|---|
| CA | 2793844 | 10/2011 |
| CA | 2800217 | 11/2012 |
| CN | 101238395 A | 8/2008 |
| CN | 101551511 A | 10/2009 |
| CN | 101632030 A | 1/2010 |
| EP | 2775961 B1 | 12/2018 |
| WO | 9011736 A1 | 10/1990 |
| WO | 20040010904 A1 | 2/2004 |
| WO | 20060023386 A2 | 3/2006 |
| WO | 20070107589 A1 | 9/2007 |
| WO | 2008024766 A2 | 2/2008 |
| WO | 2009021327 A1 | 2/2009 |
| WO | 2010103037 A1 | 9/2010 |
| WO | 2011154972 A1 | 12/2011 |
| WO | 2013016804 A1 | 2/2013 |
| WO | 2013126986 A2 | 9/2013 |
| WO | 2014121391 A1 | 8/2014 |
| WO | 2015024136 A1 | 2/2015 |
| WO | 2015066502 A1 | 5/2015 |
| WO | 2016033217 A1 | 3/2016 |
| WO | 2016161519 A1 | 10/2016 |

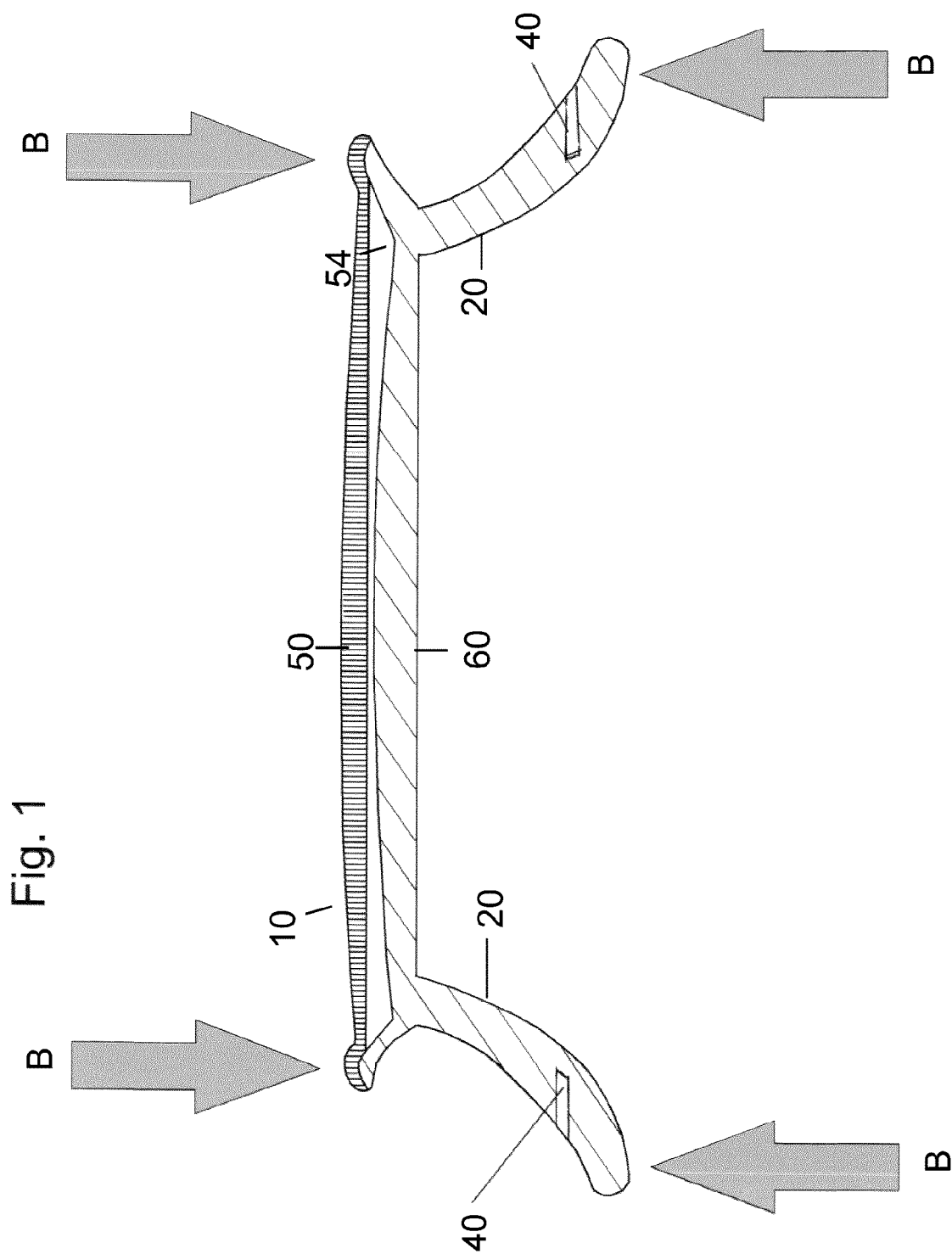

COLLAPSIBLE CAVITIES WITHIN SUSPENSION SYSTEMS FOR INTRA-OCULAR LENSES

REFERENCE TO RELATED APPLICATIONS

The present invention relates to the applicant's inflatable lens/lens retainer as disclosed in U.S. patent application Ser. No. 12/671,573 entitled INFLATABLE INTRAOCULAR LENS/LENS RETAINER filed Aug. 12, 2008, now U.S. Pat. No. 8,579,971 and pending continuation application Ser. No. 14/076,102 filed on Nov. 8, 2013, which are incorporated herein by reference in their entirety, as well as U.S. provisional application No. 61/761,569 filed Feb. 6, 2013 entitled LASER SCULPTED COMPARTMENTS WITHIN SUSPENSION SYSTEMS FOR INTRAOCUALR LENSES and international application publication no. WO 2014/121391 A1 published 14 Aug. 2014 entitled EXPANDABLE SUSPENSION SYSTEMS FOR INTRAOCULAR LENSES which are incorporated herein by this reference. The present application claims the benefits, under 35 U.S.C. § 119(e), of U.S. Provisional Application Ser. No. 62/341,430 filed May 25, 2016 entitled "Collapsible Cavities within Suspension Systems for Intra-ocular Lenses", which is incorporated herein by this reference.

TECHNICAL FIELD

The invention relates to suspension systems for accommodating intra-ocular lenses that occupy the natural lens space within the eye.

BACKGROUND

Accommodating intra-ocular lenses that have an ability to re-engage the natural kinetics of the ciliary muscle/suspensory ligament/lens capsule complex after lens extraction to allow the eye to shift focus from distance to near have emerged. Within this competitive field, much attention has focused upon an ability to insert these types of lenses through small corneo-scleral incisions within the eye. Once positioned within a vacant lens capsule located behind the pupil, the suspension systems attached to the lenses are required to expand in a controlled manner to re-establish to a functional geometric configuration of the lens capsule/suspensory ligament complex in order to facilitate a connection between movement of the ciliary muscles of the eye and a deformable optical interface within the optical element of the device. During this process, the deformable optical interface is forced into a high energy state, focusing the eye upon distant objects in space.

In the past, suspension systems have used various approaches to control their structural strength and shape recovery times. In some cases they have been too bulky and cumbersome to fit through small incisions. Additionally, it was found that even at their best, the characteristic of the suspension systems being able to retain structural strength while exhibiting very slow recovery times was not achievable. There is therefore a need for improvement in suspension system designs for accommodating intraocular lens.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems and methods which are meant to be exemplary and illustrative, not limiting in scope. In various embodiments, one or more of the above-described problems have been reduced or eliminated, while other embodiments are directed to other improvements.

One aspect of the invention provides a mechanism to control the recovery time of expandable suspension systems for accommodating intraocular lenses that comprise a hollow cavity, or a plurality of hollow cavities, having at least one opening communicating the cavity with fluid of its external environment; wherein the walls lining the cavities exhibit sufficient structural elasticity that they return toward their habitual shapes after being compressed by external force. According to one aspect, at least one wall lining the cavity may restrict the return of fluid back into the cavity. The collapsible cavity may be integrated within a supporting element or an optical element to regulate the shape recovery of structural elements that mediate the transfer of kinetic energy from the action of muscles of the eye to a deformable optical interface within the lens space behind the pupil of the eye. The collapsible cavity may be integrated within a supporting element comprising one or a plurality of legs for supporting the intra-ocular lens against an interior surface of said lens capsule.

The invention provides a suspension system for suspending an intra-ocular lens in the lens capsule of an eye, the suspension system comprising a support element, the support element comprising a surface for bearing against the inner surface of a lens capsule to thereby transmit ciliary force to the intra-ocular lens, and a collapsible cavity formed in the support element having at least one opening communicating the interior of the cavity with the adjacent space in the interior of the lens capsule to transfer fluid from the interior of the eye into and out of the collapsible cavity, wherein the support element in the vicinity of the cavity is sufficiently elastic to permit the cavity to be deformed under compression from ciliary force and to return to a rest configuration after the ciliary force is reduced.

The suspension system may comprise a plurality of collapsible cavities configured in parallel array within a supporting element for supporting the intra-ocular lens against an interior surface of the lens capsule. The collapsible cavities may each comprise lateral walls angled to the horizontal to facilitate the compression of the external opening and closing of the collapsible cavities. The lateral walls may be accommodated into a space within a horizontal wall of the collapsible cavity when compressed. The walls of the collapsible cavity may substantially close the opening to the cavity when compressed by ciliary pressure and open the opening when ciliary pressure is released, whereby at least one wall lining the collapsible cavity may function as a flap valve.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 1 is a cross-sectional view of the accommodating intraocular lens shown in FIG. 14, taken along lines A-A.

DESCRIPTION

Figure 2A:
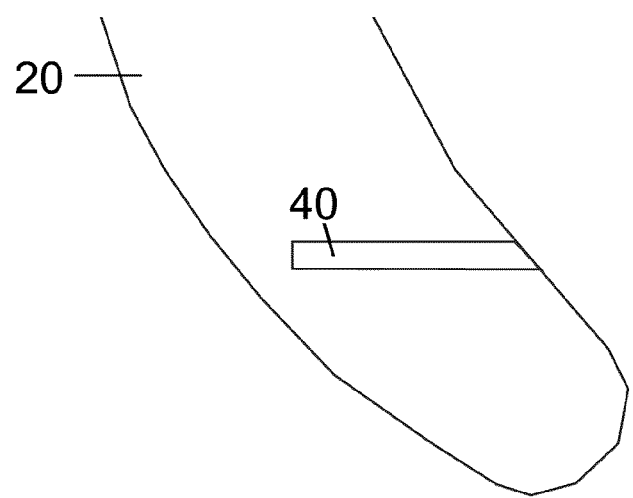
FIG. 2a is a detail cross-sectional view of a lower end of leg 20 in FIG. 1 showing a hollow cavity in its open configuration.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

FIG. 1 shows in cross-section an accommodating intraocular lens 10. Force vectors B are applied upon the accommodating lens 10 by the ciliary muscles (as described in the referenced U.S. Pat. No. 8,579,971 entitled "INFLATABLE INTRAOCULAR LENS/LENS RETAINER") to accommodate the lens to focus on distant or close objects. Lens 10 has a transparent optical element 50 supported by carriage 60 having a plurality of legs 20. A hollow space 54 is formed between optical element 50 and carriage 60. Legs 20 may be two supports 22 having broad base 24 as shown in FIG. 5-9, or multiple independent legs 26 as shown in FIG. 10-14 where eight independent legs 26 are provided on carriage 60, or other number or arrangement of legs. The lower surface of base 24 or legs 26 bears against a surface within the lens capsule, which may be the inner surface of the lens capsule to transmit the compressive force of the ciliary muscle to the accommodating lens 10.

Figure 3A:
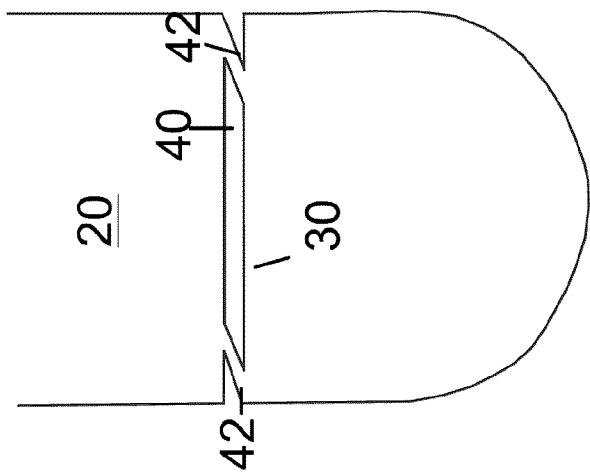
FIG. 3a is a detail front view of a lower end of leg 20 in FIG. 1 showing a hollow cavity in its open configuration.

The invention comprises hollow cavities 40 formed within the haptics or suspension systems of accommodating intraocular lenses. Within the lens capsule of the eye, the ambient ocular fluid is displaced out of a hollow cavity 40 by force generated by ciliary muscle action as show by vectors B in FIG. 1. Partial vacuums are created within hollow compartments 40 by elastic properties of the walls of the hollow cavities 40 that allow them to return to their resting state, once the force exerted by the ciliary muscles is relaxed as shown in FIGS. 2a, 3a and 4a. The return of fluid into the hollow cavities 40 is regulated by the action of a flap valve 30 which has been integrated into the architecture of at least one wall lining the hollow cavity 40. The walls of cavities 40 are structured by selection of the flexibility of the wall material and the depth and width of cavity 40 to function as a flap valve to regulate the opening and closing of the entry to cavity 40 when compressive forces are applied to leg 20.

Figure 3B:
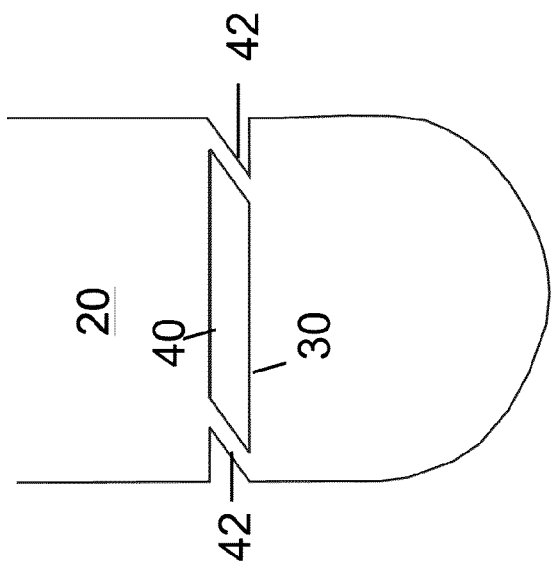
FIG. 3b is a detail front view of a lower end of leg 20 in FIG. 1 showing a hollow cavity in its closed configuration.

Certain applications for a hollow cavity within haptic regions of intraocular lenses require that the cavity return relatively slowly back to their habitual shapes, such as that described in U.S. Pat. No. 8,579,971 wherein the imbibing of liquid back into a sealed cavity having semi-permeable walls is used to control compression forces acting upon an accommodating intraocular lens. This same principle applies to hollow cavities 40 as illustrated by FIGS. 3a & 3b which illustrate an open and a closed configuration, but with more control than is attainable with the use of semi-permeable membranes in contact with liquids that establish osmotic gradients. Combinations of the use of both disparate mechanisms can be used to provide greater control of the shape of an expandable haptic.

The rate of flow of liquid into and out of a hollow cavity 40 is dependent upon a number of factors, which include but are not limited to the following; material elasticity, wall thickness, the viscosity of the fluid moving in and out of the hollow cavities, surface tension induced by the materials used to fabricate the walls of the hollow cavity, the surface area of the orifice or orifices that communicate between the interior of the hollow cavity and the surrounding fluid medium, the shape of the orifices of the hollow cavity 40, patterns created by the location of multiple hollow cavities, the efficiency of the flap valve 30 or any combination of these factors.

Figure 2B:
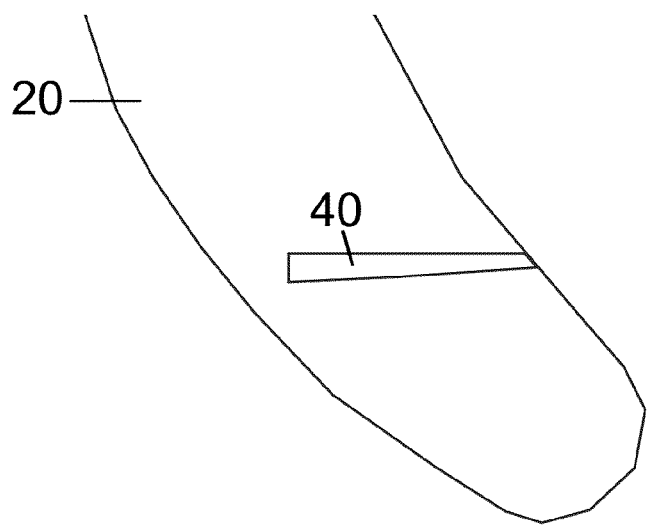
FIG. 2b is a detail cross section of a lower end of leg 20 in FIG. 1 showing a hollow cavity in its closed configuration.
Figure 4B:
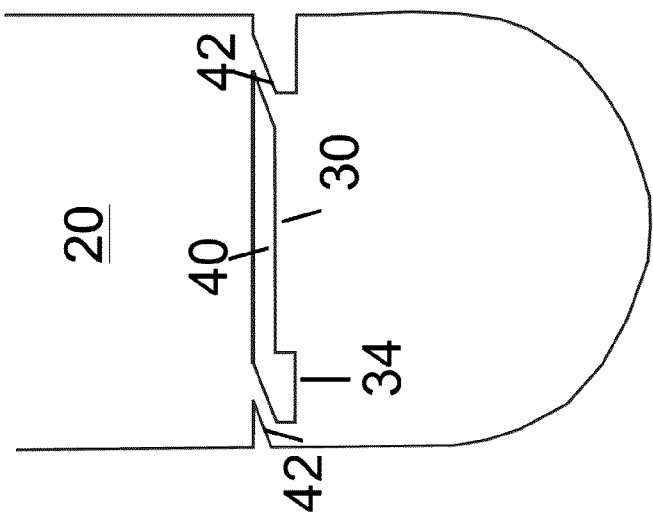
FIG. 4b is a detail front view of a lower end of leg 20 in FIG. 1 showing a second embodiment of a hollow cavity in its closed configuration.
Figure 4A:
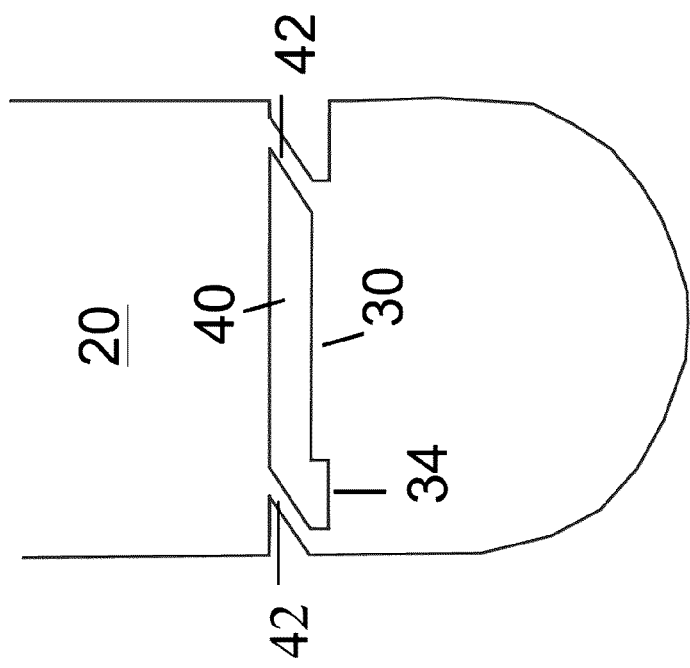
FIG. 4a is a detail front view of a lower end of leg 20 in FIG. 1 showing a second embodiment of a hollow cavity in its open configuration.
Figure 5:
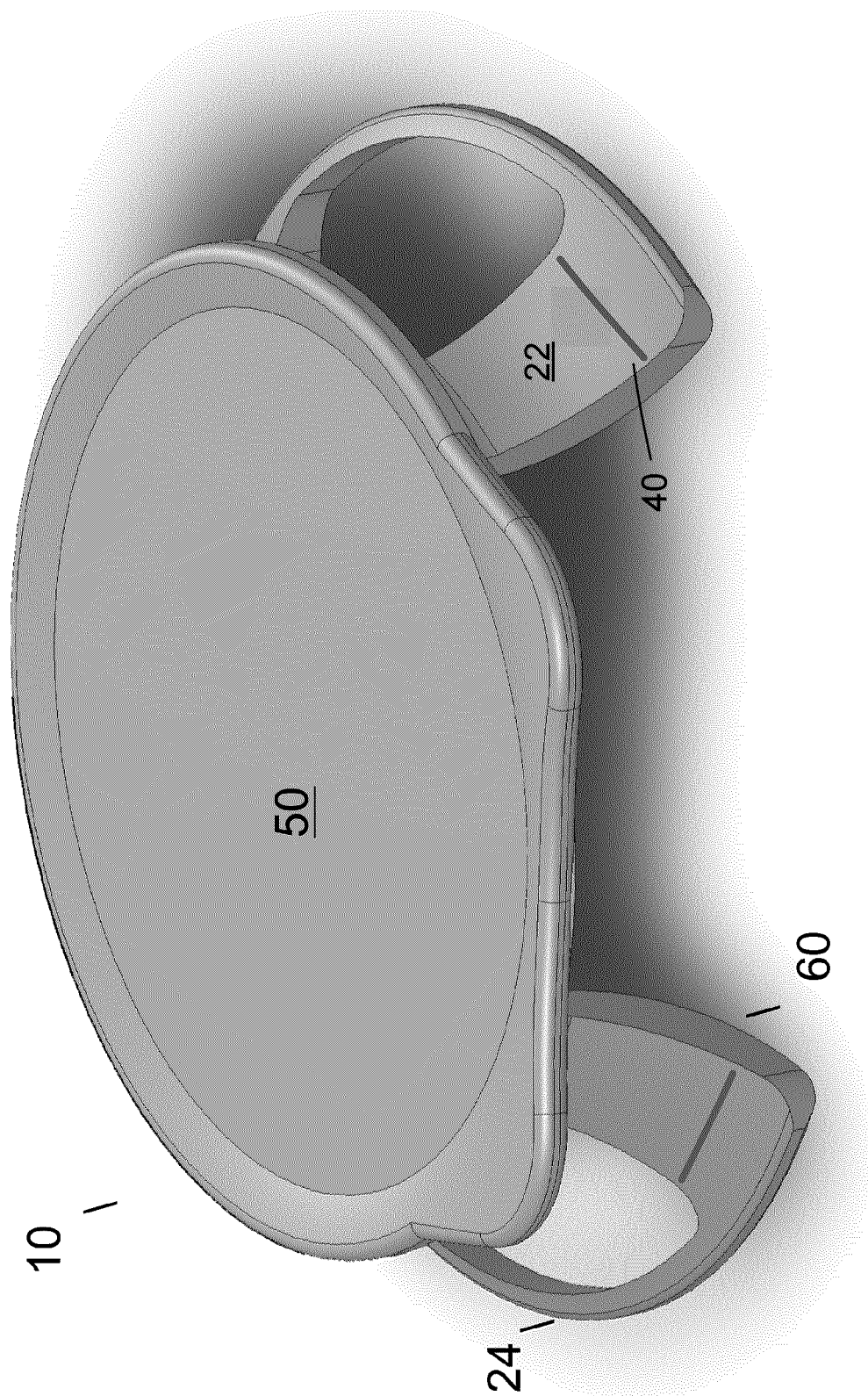
FIG. 5 is a top front perspective view of a first embodiment of an intra-ocular lens suspension system.
Figure 6:
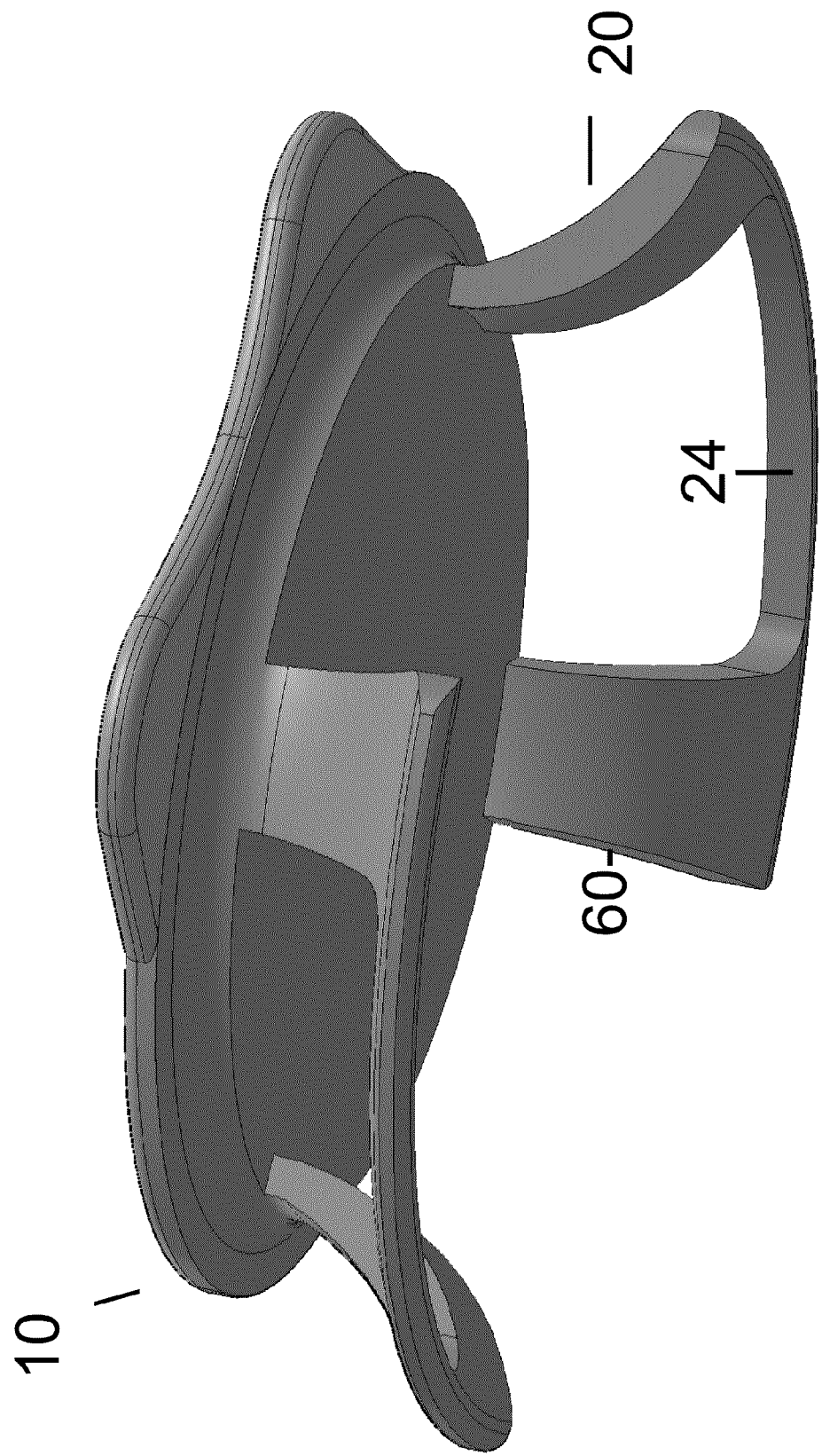
FIG. 6 is a bottom front perspective view of the embodiment shown in FIG. 5.
Figure 7:
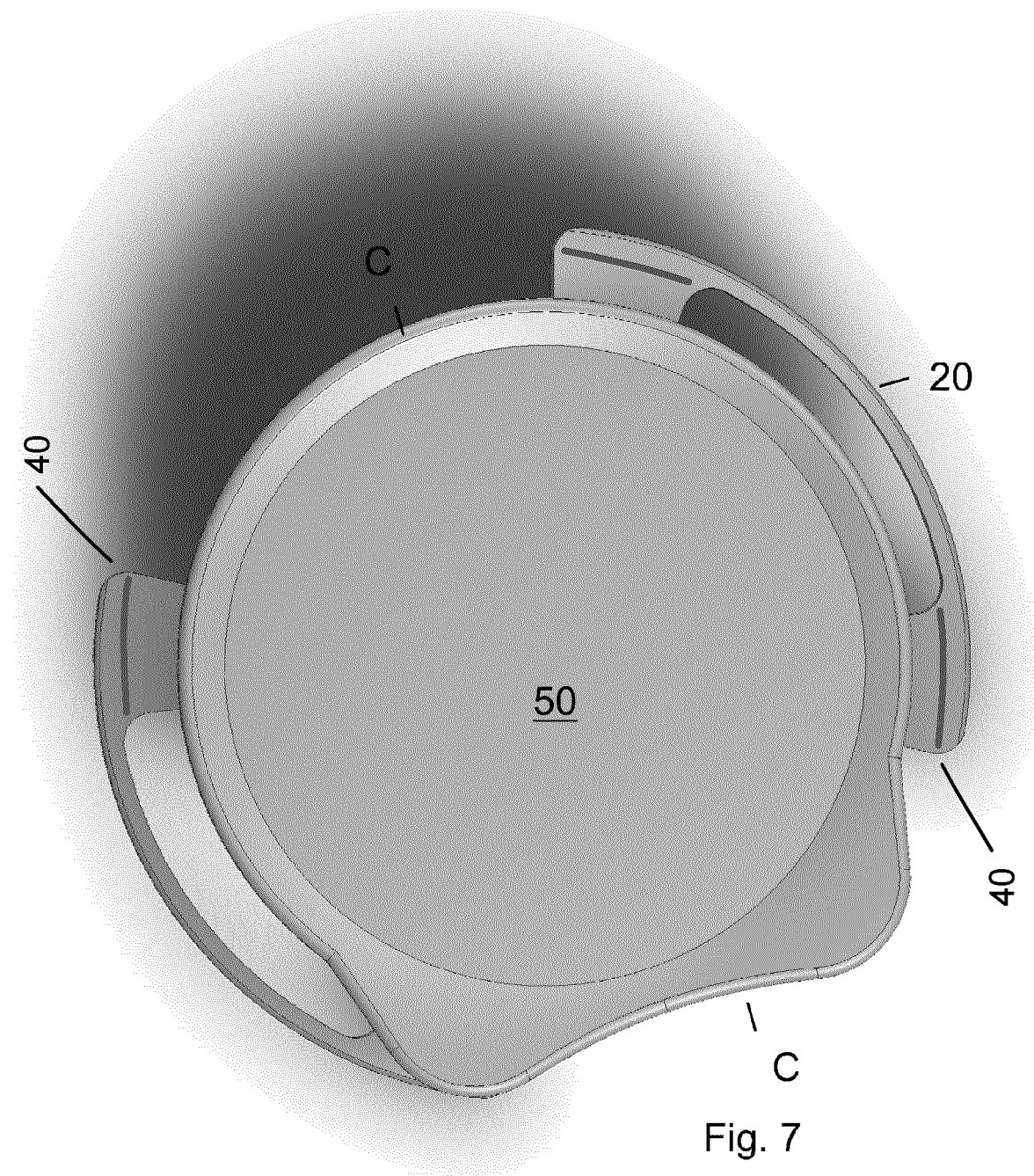
FIG. 7 is a top view of the embodiment shown in FIG. 5.
Figure 8:
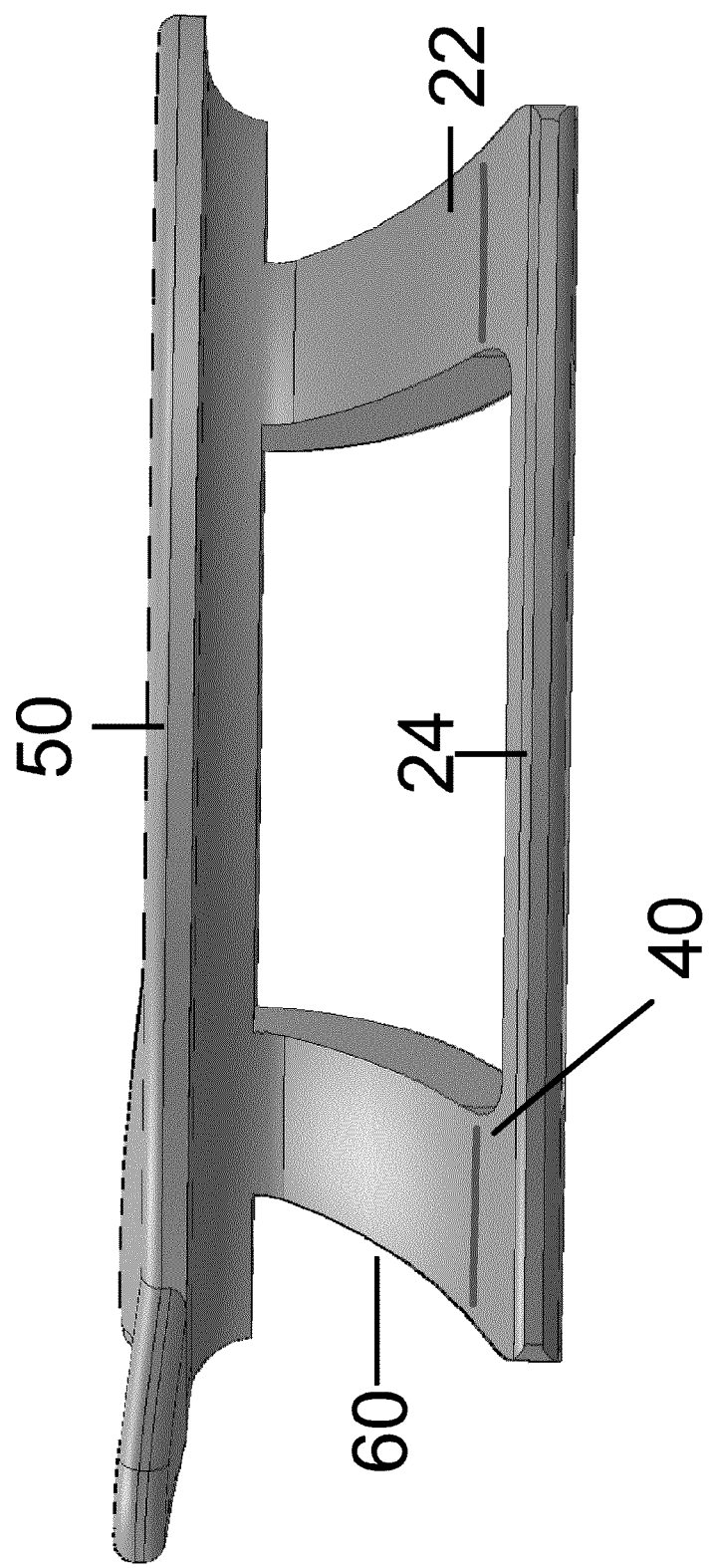
FIG. 8 is a right side view of the embodiment shown in FIG. 5.
Figure 9:
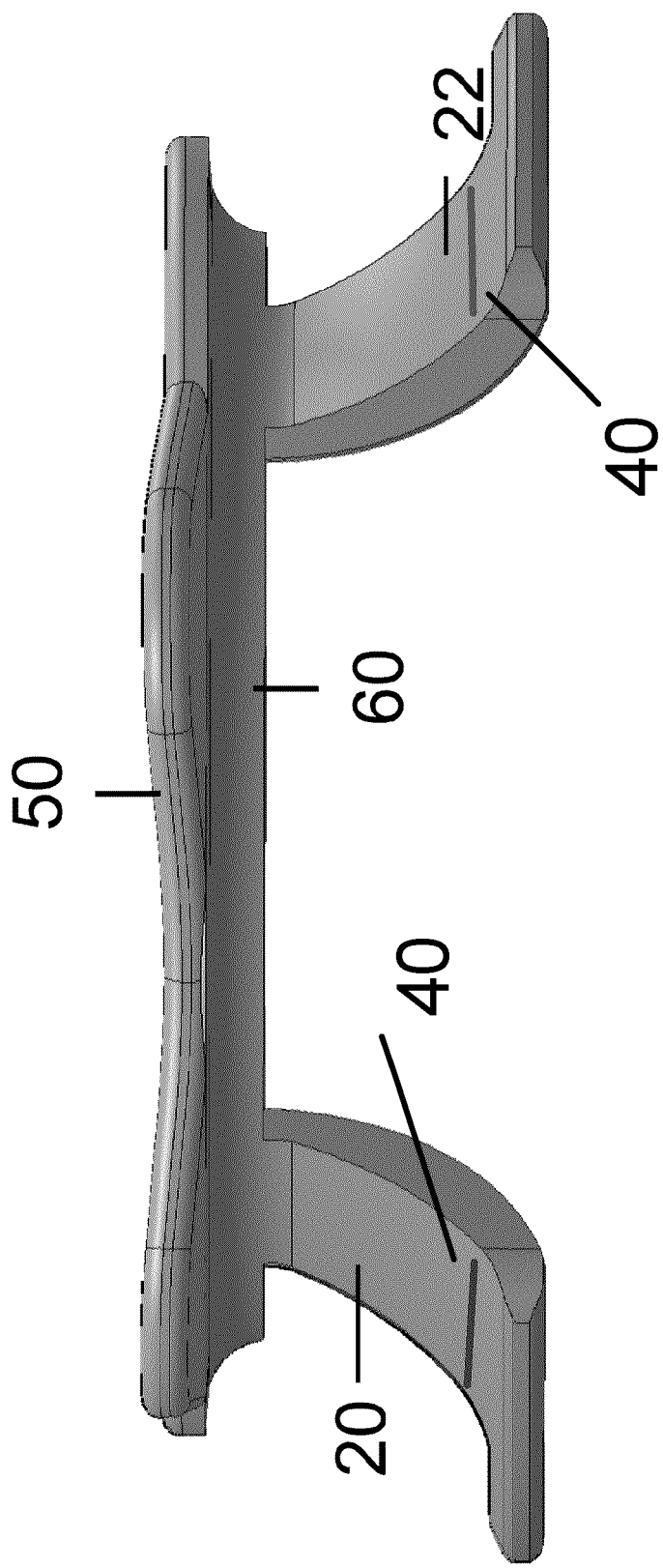
FIG. 9 is a front view of the embodiment shown in FIG. 5.
Figure 10:
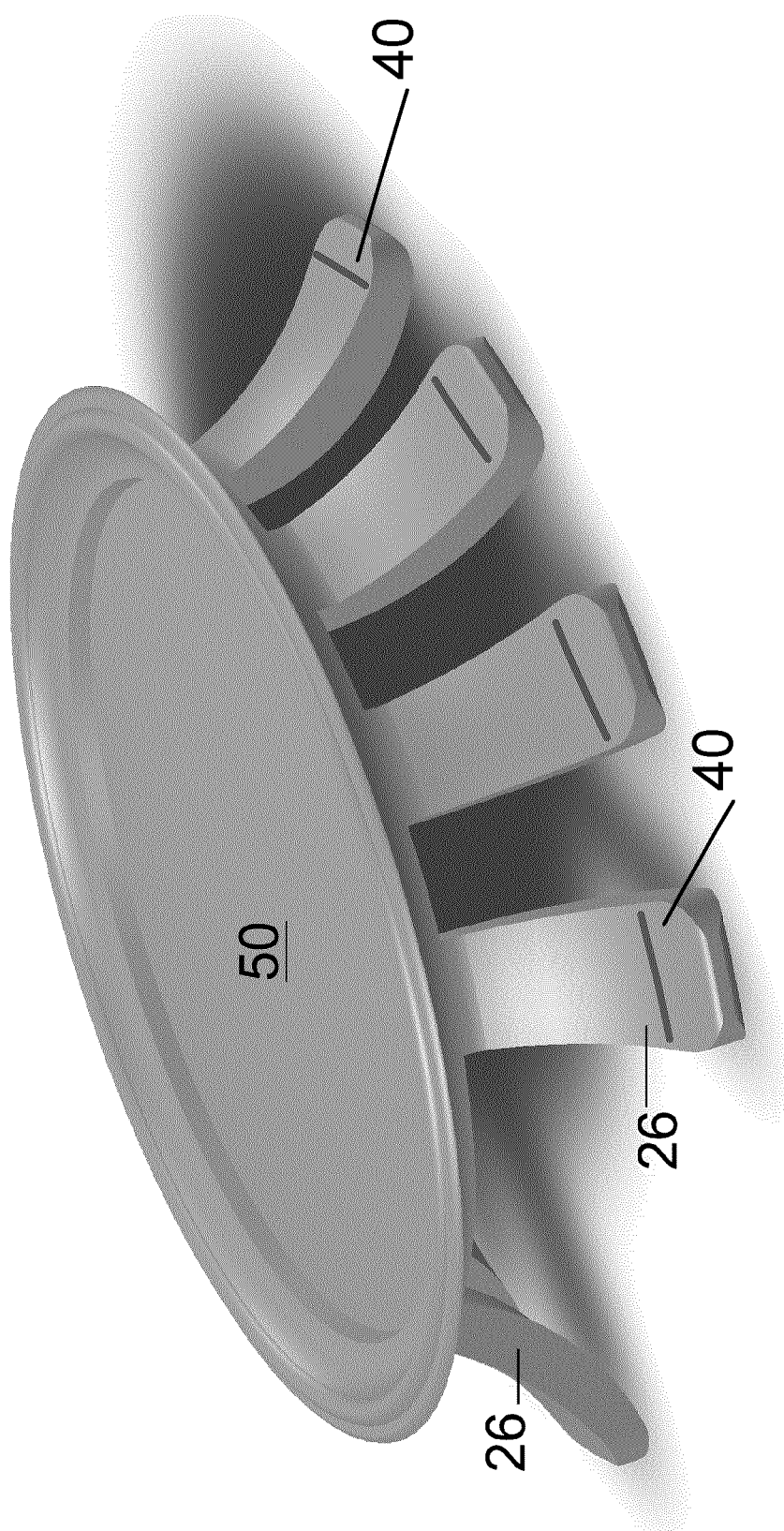
FIG. 10 is a top front perspective view of a second embodiment of an intra-ocular lens suspension system.
Figure 11:
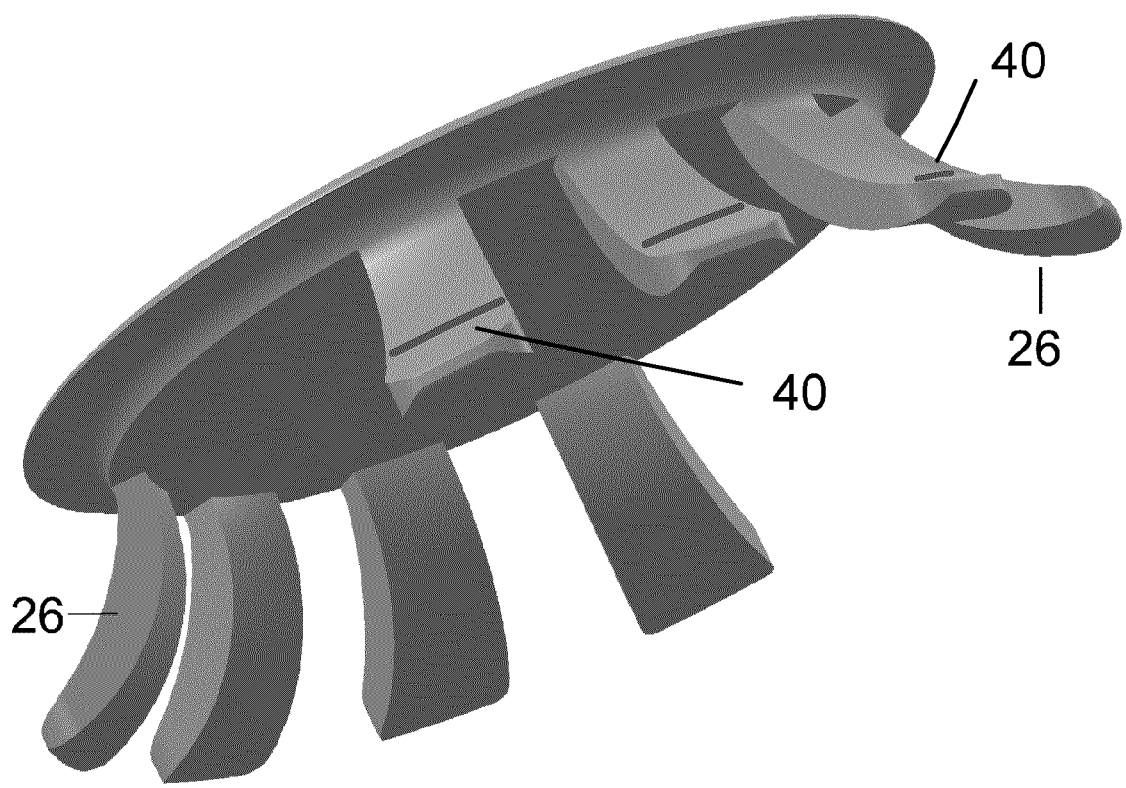
FIG. 11 is a bottom front perspective view of the embodiment shown in FIG. 10.
Figure 12:
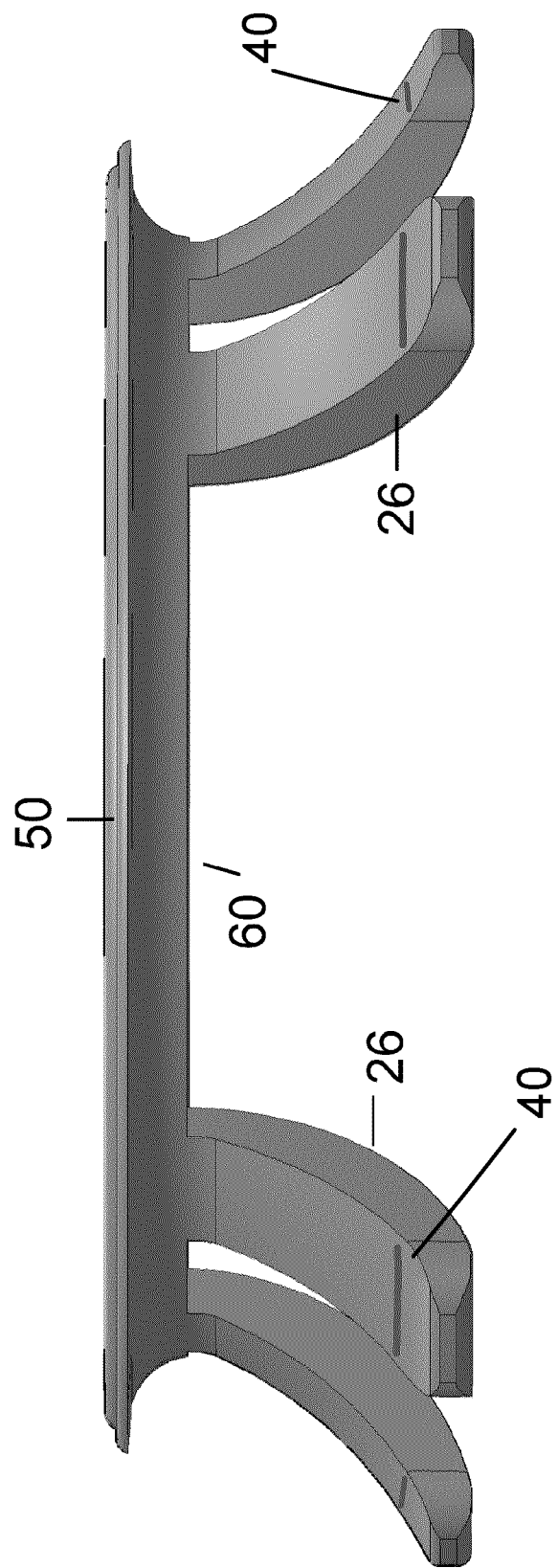
FIG. 12 is a front view of the embodiment shown in FIG. 10, the rear view being a mirror image thereof.
Figure 13:
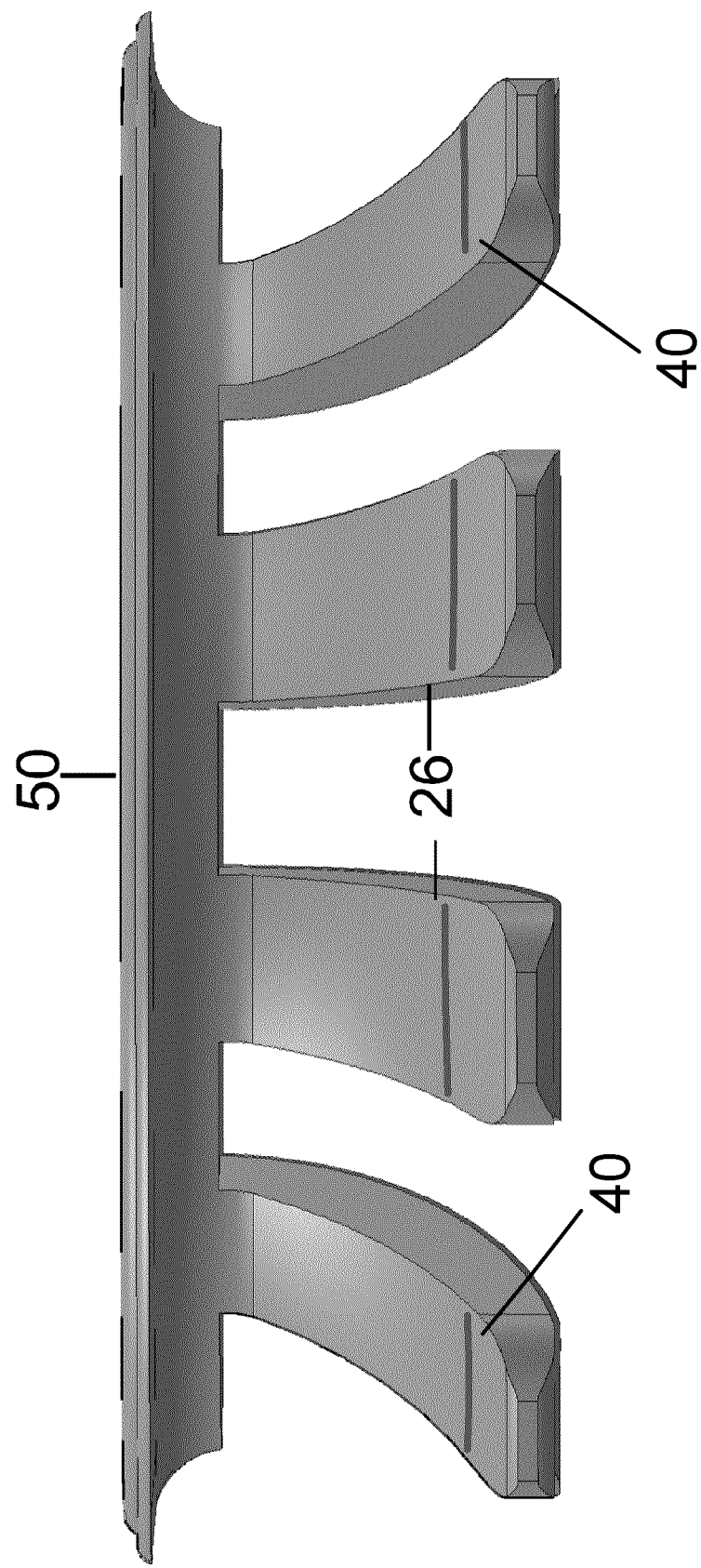
FIG. 13 is a right side view of the embodiment shown in FIG. 10, the left side view being a mirror image thereof.
Figure 14:
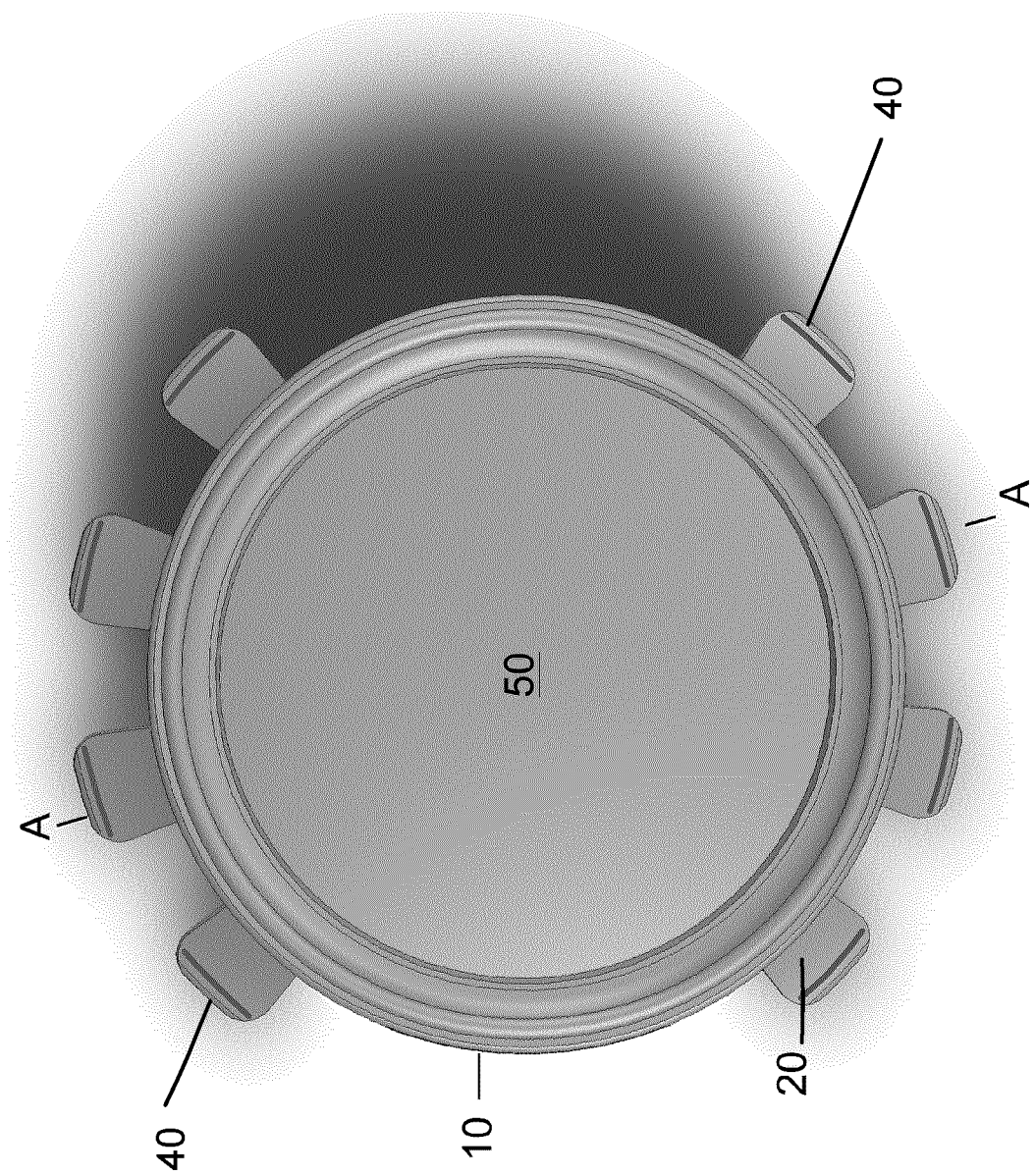
FIG. 14 is a top view of the embodiment shown in FIG. 10.

As shown in cross-section in FIGS. 1 and 2a, 2b and in front view in FIGS. 3a, 3b and 4a, 4b each hollow cavity 40 is formed as a broad slot formed in leg 20 opening to the exterior of the leg and extending radially inwardly, and which has generally parallel walls when the lens is not subjected to pressure but whose outer entry is compressed as shown in FIG. 2b, 3b, 4b when the legs 20 are subjected to compressive force. There may be one hollow cavity 40 in each leg 20 or a plurality of hollow cavities 40 may be stacked one above the other in parallel, resembling the gills of a fish when seen from the front of leg 20 and functioning as a series of flap valves, as shown in FIG. 15a, 15b, 16a, 16b. As shown in FIG. 4a, the lateral walls 42 of hollow cavities 40 may be angled at 45 degrees or similar angle relative to the horizontal, to facilitate the compression of the external opening of hollow cavity 40. FIG. 4a illustrates a modification of the design of the seating of flap valve 30, whereby the lateral wall 42 can fit into a slot 34, as shown in its closed configuration in FIG. 4b. Also, FIGS. 3a and 3b as well as 4a and 4b demonstrate the change in the width of the opening of the hollow cavities 40. The walls of hollow cavities 40 exhibit sufficient structural elasticity that they return to their habitual shapes after being compressed by external force.

Various shapes of the walls lining the hollow cavity can be formatted to customize the rate of return of liquid back into hollow cavity 40. The flap valve 30 can be configured to close completely, sealing off the inflow of liquid altogether or it can be designed to close partially to allow restricted flow, as shown in FIGS. 2a and 2b. FIGS. 2a and 2b exhibit a single hollow cavity. The present invention allows for multiple hollow cavities 40 to be stacked upon one another in a single supporting element for cumulative effect. With this stacking arrangement, the side walls of the hollow cavities 40 behave and look much like an accordion mechanism. From a frontal perspective, the flap valves appear much like fish gills, as shown in FIG. 16a, 16b, closing in response to force exerted by lens capsule compression and opening in response to the shape memory characteristics of the material substrate used to fabricate the walls lining the hollow cavity 40

Figure 15:
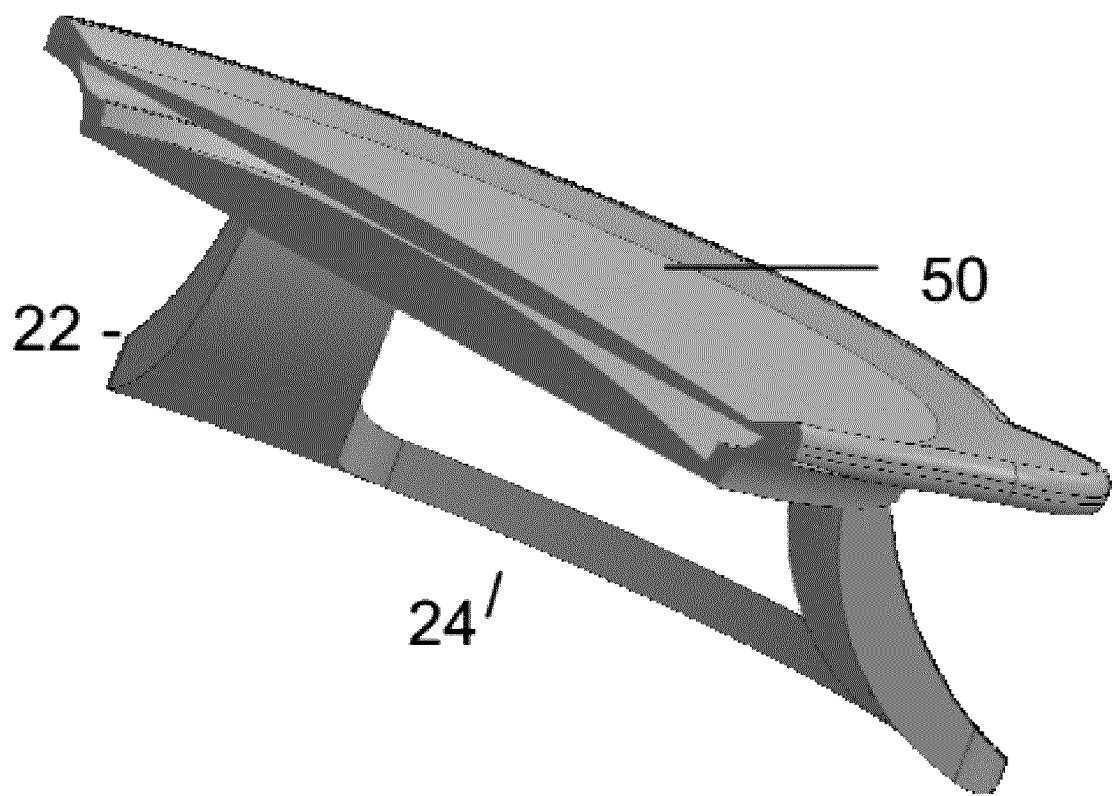
FIG. 15 is a perspective view in cross-section taken along lines C-C of FIG. 7.
Figure 15A:
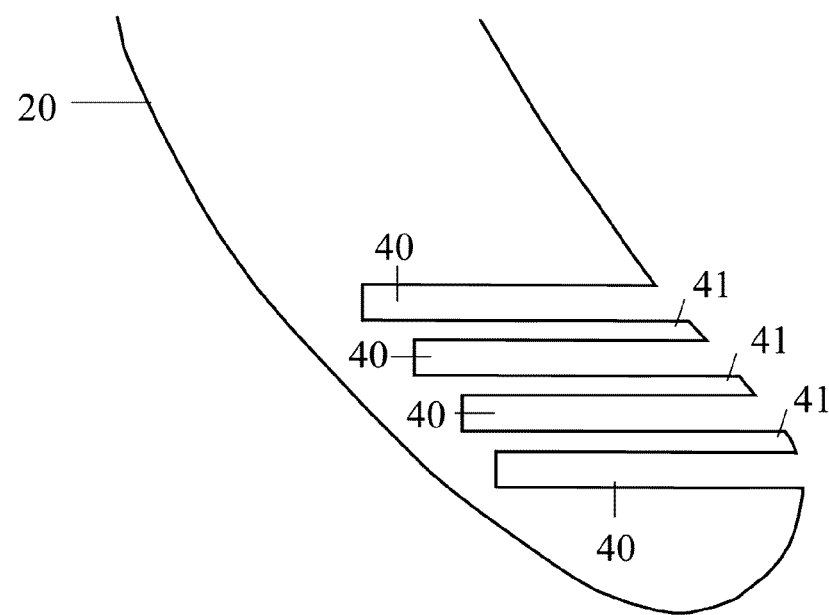
FIG. 15a is a detail cross-sectional view of a third embodiment of the lower end of leg 20 in FIG. 1 showing a plurality of parallel hollow cavities in open configuration.
Figure 15B:
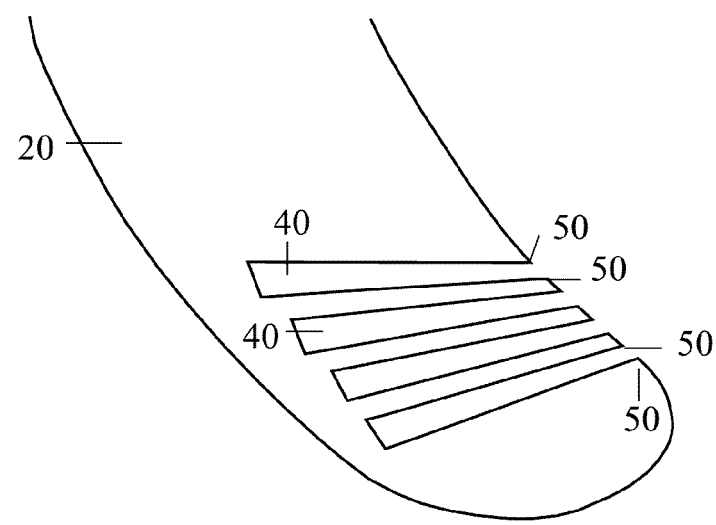
FIG. 15b is a detail cross-sectional view of the embodiment in FIG. 15a showing the hollow cavities in closed configuration.
Figure 16A:
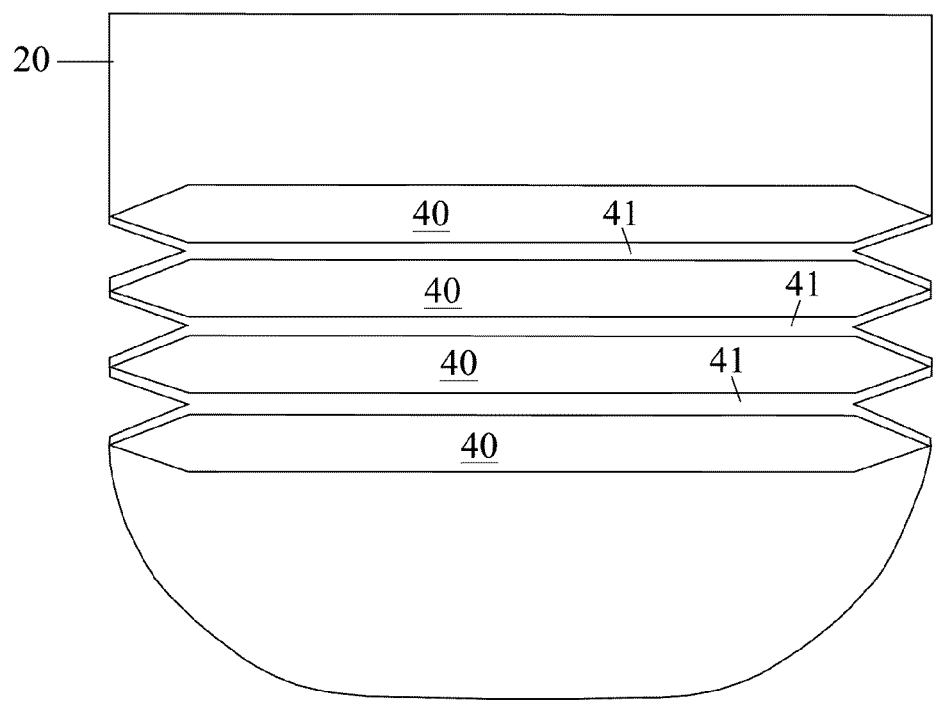
FIG. 16a is a detail front view of the embodiment of the lower end of leg 20 in FIG. 15a in open configuration.
Figure 16B:
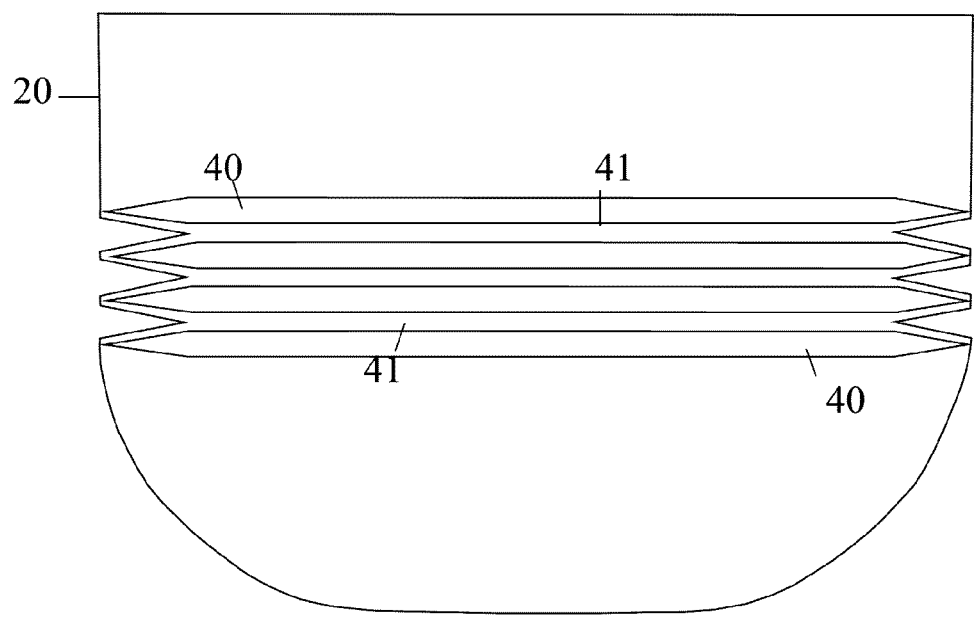
FIG. 16b is a detail front view showing the embodiment of the lower end of leg 20 in FIG. 16a in closed configuration.

As shown in cross-section in FIG. 15a and in front view in FIG. 16a, there may be provided a plurality of hollow cavities 40 stacked one above the other in parallel, resembling the gills of a fish when seen from the front of leg 20 and functioning as a series of flap valves, as shown in FIG. 15a, 15b, 16a, 16b. Again each hollow cavity 40 is formed as a broad slot formed in leg 20 opening to the exterior of the leg and extending radially inwardly, and which has generally parallel walls when the lens is not subjected to pressure but whose outer entry is compressed as shown in FIGS. 15b and 16b when the legs 20 are subjected to compressive force. In this case dividing walls 41 are formed between adjacent cavities 40. The outer edges of a slot may touch when fully compressed to seal the entry to cavity 40 or may remain slightly spaced when the leg 20 is compressed to regulate the flow of ambient fluid out of the cavity 40. Thus the walls of cavities 40 are again structured to function as a flap valve to regulate the opening and closing of the entry to cavity 40.

The materials required for the suspension elements comprising hollow cavities 40 are elastic with a strong memory, readily resuming their original size and shape after being compressed, stretched or otherwise deformed. Materials commonly used for intraocular lens fabrication having good shape memory characteristics include but are not limited to the following classifications: silicones, silicone hydro-gels, hydrophobic and hydrophilic acrylics, polyethylene, polypropylene, polyurethane and co:block polymers of these. Hollow cavities 40 are preferably laser sculpted in the carriage material but may also be formed by molding, carving or the like.

By providing hollow cavities in the carriage 60 of the intra-ocular lens 10, compressive forces allow the lens to accommodate adjustment to the optical element 50 while having the ability to recover the original shape of the lens quickly when the compressive force is released. The specific configuration of the supporting legs 20 of carriage 60 in the disclosed embodiment, which provide a concave upwardly facing profile (as shown in cross-section in FIG. 1 and in side view in FIG. 15), rather than a convex upwardly facing profile, has been found particularly effective for absorbing and communicating the compressive force of the ciliary muscles. While the present invention has been illustrated in connection with specific embodiments of an accommodating intraocular lens, however, it can be integrated broadly within any optical element or suspension system that links ciliary muscle action with curvature or refractive change within the lens space behind the pupil.

Collapsible cavities as described above may also be integrated within the optical element 50 or other optical element to regulate the shape recovery of structural elements that mediate the transfer of kinetic energy from the action of the ciliary muscles of the eye to a deformable optical interface within the lens space behind the pupil of the eye.

The shape recovery characteristics of the present invention provide a means whereby structural elements placed within the lens space inside the human eye can be oriented to efficiently harness kinetic energy initiated by ciliary muscle movement through its connection with the zonular/lens capsule complex. This efficiency can be exploited to induce curvature change for various designs of accommodating lenses but it can also be used to control and/or generate electrical current.

Various electro-mechanical lens designs having alterable optical properties have recently emerged. In general they change curvature or refractive index in response to the flow of an electrical current. The flow of electricity within the eye can be regulated by electrical switches placed between the lens capsule and structural elements of the subject suspension system. Similarly, electrical current can be generated by micro-sized electrical generators placed between the lens capsule and structural elements of the suspension system. With the use of an expandable lens suspension system within the lens space of the eye, ciliary muscle action can be transferred via the zonular/lens capsule complex to activate a wide array of such electrical components.

The present invention thus can efficiently harness kinetic energy derived from movement of the zonular/lens capsule complex for a variety of mechanical and electrical adaptations that can generate or alter light that ultimately impinges upon the retina of each recipient eye.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A suspension system for suspending an intra-ocular lens in the lens capsule of an eye, said suspension system comprising a support element, said support element comprising a surface for bearing against the inner surface of a lens capsule to thereby transmit ciliary force to said intra-ocular lens, and a collapsible cavity formed in said support element having at least one opening communicating the interior of said cavity with the adjacent space in the interior of the lens capsule to allow fluid to flow from the interior of the lens capsule into and out of said collapsible cavity, said collapsible cavity having walls lining said cavity, wherein said support element in the vicinity of said collapsible cavity is sufficiently elastic to permit said cavity to be deformed under compression from said ciliary force and to return to a rest configuration after said ciliary force is reduced and wherein the flow of fluid into and out of said collapsible cavity is regulated by a flap valve action of said walls lining said collapsible cavity, whereby compression of said cavity causes the distance separating said walls to be reduced to a greater extent in the vicinity of said opening than in a location in said cavity spaced from said opening to thereby restrict the flow of fluid back into said cavity after said ciliary force is reduced.

2. The suspension system of claim 1 wherein said flap valve action of said walls lining said collapsible cavity comprises a flap valve action of at least one wall lining said collapsible cavity.

3. The suspension system of claim 1 wherein said walls of the collapsible cavity reversibly restrict the cross-sectional area of said opening to the cavity when compressed by ciliary pressure to thereby restrict the flow of fluid from said collapsible cavity when compressed by ciliary pressure.

4. The suspension system of claim 1 wherein said flow of fluid into and out of said collapsible cavity is regulated by said walls lining said collapsible cavity being deformed under compression from said ciliary force to restrict the return of fluid into and out of said cavity.

5. The suspension system of claim 1 wherein said collapsible cavity comprises opposed upper and lower planar walls and said flow of fluid into and out of said collapsible cavity is regulated by the distance between said opposed planar walls being reversibly reduced under compression from said ciliary force to a greater extent in the vicinity of said opening than in a location in said cavity spaced from said opening to restrict the flow of fluid out of said cavity while under compression from said ciliary force and back into said cavity when compression is reduced.

6. The suspension system of claim 1 wherein said collapsible cavity comprises a slot formed in said support element opening to the exterior of said support element and extending inwardly from the exterior of said support element, and which comprises generally two parallel walls when said support element is not subjected to ciliary pressure and wherein said opening is constricted when said support element is subjected to compression from said ciliary force causing a relative movement of said generally parallel walls to reduce the spacing of said generally parallel walls in the vicinity of said opening.

7. The suspension system of claim 1 wherein the flow of fluid into and out of said collapsible cavity is regulated by the relative movement of at least two opposed walls lining said collapsible cavity to thereby pinch more closely together said two opposed walls in the vicinity of said opening than in a location in said cavity spaced from said opening.

8. The suspension system of claim 1 wherein the walls of said collapsible cavity substantially close the opening to said cavity when compressed by ciliary pressure and said opening is returned to its open configuration at rest when said ciliary pressure is released.

9. The suspension system of claim 1 wherein said support element comprises a plurality of collapsible cavities configured in a parallel array in said support element for supporting said intraocular lens against an interior surface of said lens capsule.

10. The suspension system of claim 9 wherein said walls lining each said collapsible cavity of said parallel array restrict the flow of fluid out of and back into said collapsible cavity when each said collapsible cavity is deformed.

11. The suspension system of claim 1 wherein at least one wall of said collapsible cavity acts as a flap valve to partially or substantially close the opening to said cavity when compressed by ciliary pressure and partially or substantially open said opening when said ciliary pressure is released.

12. The suspension system of claim 1 wherein said collapsible cavity comprises opposed walls which are caused by said flap valve action to be relatively angled to facilitate the regulation of the size of the opening of said collapsible cavity when ciliary pressure is applied to or released from said support element.

13. The suspension system of claim 1 wherein said suspension system comprises a plurality of collapsible cavities each comprising opposed walls which are caused by said flap valve action to be relatively angled to reduce the size of the opening of said collapsible cavity when compressed by ciliary pressure.

14. The suspension system of claim 1 wherein said collapsible cavity comprises a horizontal surface provided with one or more depressions into which one of said opposed walls is accommodated when said collapsible cavity is compressed.

15. The suspension system of claim 1 wherein said flow of fluid into and out of said collapsible cavity is regulated by said walls lining said collapsible cavity being deformed under compression from said ciliary force to restrict the return of fluid back into said cavity.

16. The suspension system of claim 1 further comprising an optical element comprising a deformable optical interface and wherein said collapsible cavity is integrated within said support element for said optical element to regulate the shape recovery of structural elements that act to transfer kinetic energy from the action of ciliary muscles of an eye to said deformable optical interface.

17. The suspension system of claim 1 wherein said support element comprises a plurality of legs for supporting said intra-ocular lens against an interior surface of said lens capsule.

* * * * *